US010183106B2

(12) United States Patent
Okabe et al.

(10) Patent No.: US 10,183,106 B2
(45) Date of Patent: Jan. 22, 2019

(54) BLOOD PURIFICATION SYSTEM

(71) Applicant: Nikkiso Company Limited, Tokyo (JP)

(72) Inventors: Harutoshi Okabe, Makinohara (JP); Hiroaki Suzuki, Makinohara (JP); Masaru Kuchiki, Makinohara (JP)

(73) Assignee: Nikkiso Company Limited, Tokyo (JP)

( * ) Notice: Subject to any disclaimer, the term of this patent is extended or adjusted under 35 U.S.C. 154(b) by 267 days.

(21) Appl. No.: 14/093,437

(22) Filed: Nov. 30, 2013

(65) Prior Publication Data

US 2014/0083917 A1 Mar. 27, 2014

Related U.S. Application Data

(63) Continuation of application No. PCT/JP2012/064129, filed on May 31, 2012.

(30) Foreign Application Priority Data

Jun. 1, 2011 (JP) ................................ 2011-123391

(51) Int. Cl.
*A61M 1/16* (2006.01)

(52) U.S. Cl.
CPC ............ *A61M 1/1656* (2013.01); *A61M 1/16* (2013.01); *A61M 1/1601* (2014.02); *A61M 1/168* (2013.01); *A61M 1/1654* (2013.01); *A61M 1/1682* (2014.02); *A61M 1/169* (2013.01); *A61M 2205/3317* (2013.01); *A61M 2205/3324* (2013.01); *A61M 2205/3331* (2013.01); *A61M 2205/3561* (2013.01); *A61M 2205/3584* (2013.01); *A61M 2205/502* (2013.01); *A61M 2205/84* (2013.01)

(58) Field of Classification Search
USPC ................................ 210/140, 142, 143, 96.2
See application file for complete search history.

(56) References Cited

U.S. PATENT DOCUMENTS

| 4,596,549 | A | * | 6/1986 | Minami ................. A61M 1/16 210/140 |
| 5,015,389 | A | * | 5/1991 | Portillo, Jr. ......... A61M 1/1656 210/646 |
| 5,346,472 | A | | 9/1994 | Keshaviah et al. |
| 6,126,831 | A | | 10/2000 | Goldau et al. |
| 2003/0080059 | A1 | | 5/2003 | Peterson et al. |
| 2004/0057037 | A1 | | 3/2004 | Ohishi et al. |

(Continued)

FOREIGN PATENT DOCUMENTS

| JP | 59-41428 | 3/1984 |
| JP | 1-232970 | 9/1989 |

(Continued)

*Primary Examiner* — Dirk R Bass
(74) *Attorney, Agent, or Firm* — Harness, Dickey & Pierce, P.L.C.

(57) ABSTRACT

A blood purification system includes a plurality of monitoring devices (1) each attached to a dialyzer (5) to perform a blood purification treatment on a patient. A dialysate supplying device (2) supplies a dialysate to each of the monitoring devices (1). The plurality of monitoring devices (1) and the dialysate supplying device (2) are connected to each other by a LAN cable α. Thus, predetermined individual information relating to the plurality of monitoring devices (1) is transmitted from each of the monitoring devices (1) to the dialysate supplying device (2).

18 Claims, 8 Drawing Sheets

(56) References Cited

U.S. PATENT DOCUMENTS

| | | |
|---|---|---|
| 2008/0312960 A1 | 12/2008 | Nikolic et al. |
| 2010/0010426 A1 | 1/2010 | Childers et al. |
| 2010/0181235 A1 | 7/2010 | Fava et al. |
| 2012/0175296 A1* | 7/2012 | Wehmeyer .......... A61M 1/1654 210/321.69 |

FOREIGN PATENT DOCUMENTS

| | | |
|---|---|---|
| JP | 5-33063 | 5/1993 |
| JP | 6-9668 | 3/1994 |
| JP | 8-280794 | 10/1996 |
| JP | 2004-016412 | 1/2004 |
| JP | 2004-358269 | 12/2004 |
| JP | 2005-124775 | 5/2005 |
| JP | 2007-236532 | 9/2007 |
| JP | 2008-023324 | 2/2008 |
| JP | 4051560 | 2/2008 |
| JP | 4129866 | 8/2008 |
| JP | 4164165 | 10/2008 |
| JP | 4304711 | 7/2009 |
| JP | WO2010-006146 | 1/2010 |
| JP | 4536143 | 9/2010 |
| JP | 4548349 | 9/2010 |
| WO | WO2005/025726 | 3/2005 |

\* cited by examiner

BLOOD PURIFICATION SYSTEM

CROSS-REFERENCE TO RELATED APPLICATIONS

This application is a continuation of International Application No. PCT/JP2012/064129, filed May 31, 2012, which claims priority to Japanese Application No. 2011-123391, filed Jun. 1, 2011. The disclosures of the above applications are incorporating herein by reference.

FIELD

The present disclosure relates to a blood purification system that includes multiple blood purification mechanisms that is attached to a blood purifier that performs a blood purification treatment on a patient and a supplying mechanism capable of supplying a dialysate or an undiluted dialysate to each of the blood purification mechanisms.

BACKGROUND

In general, a blood purification system is configured such that a dialysate supplying device is installed in a machine room in a medical facility, such as a hospital. A dialysis monitoring device is installed in a separately arranged dialysis room (treatment room). The dialysate supplying device and the dialysis monitoring device are connected to each other by a pipe. The dialysate supplying device produces a dialysate with a predetermined concentration by using supplied clean water. A plurality of dialysis monitors is installed. The monitors correspond to the number of blood purifiers (dialyzers) that perform dialysis treatments on patients, introduce the dialysate produced by the dialysate supplying device through the pipe, and supply the dialysate to the blood purifiers.

A configuration is made such that the dialysate is distributed and fed from the dialysate supplying device, installed in the machine room, to the plurality of dialysis monitoring devices, installed in the dialysis room. The dialysate is supplied to the dialyzers in each dialysis monitoring device. A blood purification system that distributes the dialysate produced in the machine room as described above to each dialysis monitoring device is generally referred to as a "central system for a dialysis treatment". A device that can produce the dialysate for each of the blood purifiers (that is, each dialysis treatment patient) is generally referred to as a "personal dialysis device".

In the related art, a technique has been suggested where the dialysate supplying device and each of the dialysis monitoring devices are electrically connected to each other. During a dialysis treatment process, a pipe cleaning process or a pipe disinfecting process, an electrical signal (process signal) is transmitted from the dialysate supplying device (supplying mechanism) to each of the dialysis monitoring devices (blood purification mechanism). In this manner, each of the dialysis monitoring devices, when receiving a predetermined electrical signal (process signal), performs an operation (driving of a pump or opening and closing of an electromagnetic valve) corresponding to the signal. See, Japanese Unexamined Patent Application Publication No. 2004-16412.

However, in the above-described blood purification system, the electrical signal is unilaterally transmitted from the dialysate supplying device (supplying mechanism) to each of the dialysis monitoring devices (blood purification mechanisms). Thus, a problem exists in that it is difficult to accurately determine an actual condition of the dialysis monitors. Similarly, such a problem also arises when the blood purification mechanism is adapted to the personal dialysis device.

SUMMARY

The present disclosure is made in view of such circumstances, and aims to provide a blood purification system that can accurately determine an actual condition of a blood purification mechanism and instruct a supplying mechanism to perform an operation.

According to the disclosure, a blood purification system includes multiple blood purification mechanisms, attached to a blood purifier, to perform a blood purification treatment on a patient. A supplying mechanism is also provided. The supplying mechanism is capable of supplying a dialysate, an undiluted dialysate, clean water or an antiseptic solution to each of the blood purification mechanisms. Thus, predetermined individual information relating to the multiple blood purification mechanisms can be transmitted to the supplying mechanism.

In the blood purification system, the predetermined information includes information relating to temperature, pressure, concentration, flow rate, or time of a liquid that is supplied from the supplying mechanism to the blood purification mechanism.

In the blood purification system, the supplying mechanism is adapted to have a dialysate supplying device that can produce a dialysate with a predetermined concentration by using clean water and an undiluted dialysate. The blood purification mechanism includes a monitoring device that supplies the dialysate, supplied from the dialysate supplying device, to the blood purifier.

In the blood purification system, the supplying mechanism includes a water treatment device that produces clean water. The blood purification mechanism includes a personal dialysis device that produces a dialysate with a predetermined concentration, by using the clean water supplied from the water treatment device. Also, it supplies the dialysate to the blood purifier.

In the blood purification system, the supplying mechanism includes a water treatment device, that produces clean water, and a dissolving device, that produces an undiluted dialysate with predetermined concentration by using the clean water produced in the water treatment device. The blood purification mechanism includes a personal dialysis device that produces a dialysate with a predetermined concentration and supplies the dialysate to the blood purifier. The undiluted dialysate and the clean water, respectively supplied from the dissolving device and the water treatment device, produce the dialysate.

In the blood purification system, a predetermined operation is performed by the supplying mechanism when the predetermined information is transmitted from the blood purification mechanism.

In the blood purification system, the predetermined information is requirement information or permission information that requires or permits cleaning or disinfecting of a pipe in the blood purification mechanism.

In the blood purification system, information relating to an amount of the dialysate to be used in each of the blood purification mechanisms is transmitted from the blood purification mechanisms to the supplying mechanism.

In the blood purification system, based on the amount of the dialysate to be used, that is transmitted from the blood purification mechanisms, the supplying mechanism produces the dialysate or the undiluted dialysate, instructs the producing or dialysate, or sends a notification to prompt the producing of dialysate.

In the blood purification system, information relating to an amount of cleaning water and an antiseptic solution or a displacing liquid that is required by each of the blood purification mechanisms is transmitted from the blood purification mechanisms to the supplying mechanism.

In the blood purification system, based on the required amount of the cleaning water, the antiseptic solution, or the displacing liquid that is transmitted from the blood purification mechanisms, the supplying mechanism supplies the cleaning water or the antiseptic solution.

In the blood purification system, the supplying mechanism can display a history relating to cleaning, disinfecting or displacing in each blood purification mechanism.

In the blood purification system, the supplying mechanism can detect an abnormality by comparing information of a liquid to be supplied to the blood purification mechanisms with the predetermined information transmitted from the blood purification mechanisms.

In the blood purification system, the supplying mechanism and the blood purification mechanisms can bilaterally communicate with each other.

According to the disclosure, the predetermined individual information relating to the multiple blood purification mechanisms can be transmitted from each of the blood purification mechanisms to the supplying mechanism. Therefore, an actual condition of each of the blood purification mechanisms can be accurately understood. The supplying mechanism performs an operation.

The predetermined information includes the information relating to temperature, pressure, concentration, flow rate or time of the liquid that is supplied from the supplying mechanism to the blood purification mechanisms. Therefore, real-time information in the blood purification mechanisms can be transmitted to the supplying mechanism. Thus, the actual condition of the blood purification mechanisms can be more accurately determined.

The supplying mechanism has the dialysate supplying device that can produce the dialysate, with a predetermined concentration by using clean water, and the undiluted dialysate. The blood purification mechanism has the monitoring device that supplies the dialysate supplied from the dialysate supplying device to the blood purifier. Therefore, the blood purification mechanism can be applied to a central system.

The supplying mechanism has the water treatment device that can produce clean water. The blood purification mechanisms, have personal dialysis devices that produce the dialysate, with predetermined concentration by using the clean water supplied from the water treatment device. Also, it supplies the dialysate to the blood purifier. Therefore, the blood purification system can be applied to a blood purification system with a personal dialysis device.

The supplying mechanism has the water treatment device and the dissolving device. The water treatment device can produce clean water. The dissolving device can produce the undiluted dialysate, with a predetermined concentration by using the clean water produced in the water treatment device. The blood purification mechanisms have a personal dialysis device that produces the dialysate with a predetermined concentration, by using the undiluted dialysate and the clean water. They are, respectively, supplied from the dissolving device and the water treatment device. The devices supply the dialysate to the blood purifier. Therefore, the blood purification system can be applied to a blood purification system with personal dialysis devices.

When the predetermined information is transmitted from the blood purification mechanism, a predetermined operation is performed by the supplying mechanism. Therefore, various operations can be performed by giving priority to a condition of the blood purification mechanism. This further improves operation.

The predetermined information is the required information or the permission information that requires or permits cleaning or disinfecting of the pipe in the blood purification mechanism. Therefore, it is possible to further improve the operation during cleaning or disinfecting.

The information relating to the amount of the dialysate to be used in each of the blood purification mechanisms is transmitted from the blood purification mechanisms to the supplying mechanism. Therefore, the actual condition of the blood purification mechanisms can be accurately determined. Also, the dialysate or the undiluted dialysate can be supplied by the supplying mechanism.

Based on the amount of the dialysate to be used, which is transmitted from the blood purification mechanisms, the supplying mechanism produces the dialysate or the undiluted dialysate, instructs the producing or the dialysates, or sends the notification to prompt the producing of the dialysate. Therefore, it is possible to produce a more appropriate amount of the dialysate or the undiluted dialysate.

The information relating to the amount of cleaning water, the antiseptic solution or the displacing liquid that is required by each of the blood purification mechanisms is transmitted from the blood purification mechanism to the supplying mechanism. Therefore, the actual condition of the blood purification mechanism can be accurately determined. Also, the cleaning water or the antiseptic solution can be supplied by the supplying mechanism.

Based on the required amount of the cleaning water, the antiseptic solution or the displacing liquid that is transmitted from the blood purification mechanisms, the supplying mechanism supplies the cleaning water or the antiseptic solution. Therefore, it is possible to produce a more appropriate amount of the cleaning water or the antiseptic solution.

The supplying mechanism can display the history relating to cleaning, disinfecting or displacing in each blood purification mechanisms. Therefore, it is possible to determine overall confirmation as to whether or not the cleaning or the disinfecting of each blood purification mechanism has been satisfactorily performed. Thus, compared to a case of visually and respectively confirming the histories displayed on each blood purification mechanism, it is possible to improve workability.

The supplying mechanism can detect abnormalities by comparing information of the liquid to be supplied to the blood purification mechanism with the predetermined information transmitted from the blood purification mechanism. Therefore, more precise self-diagnosis can be performed. Also, reliability of the blood purification system can be improved further. Thus, it is possible to eliminate a need for an individual sensor for the self-diagnosis.

The supplying mechanism and the blood purification mechanisms can bilaterally communicate with each other. Therefore, various items of the information can be communicated between the supplying mechanism and the blood purification mechanisms. Thus, it is possible to perform a more appropriate blood purification treatment.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

DETAILED DESCRIPTION

Hereinafter, an embodiment of the present disclosure will be described in detail with reference to the drawings.

Figure 1:
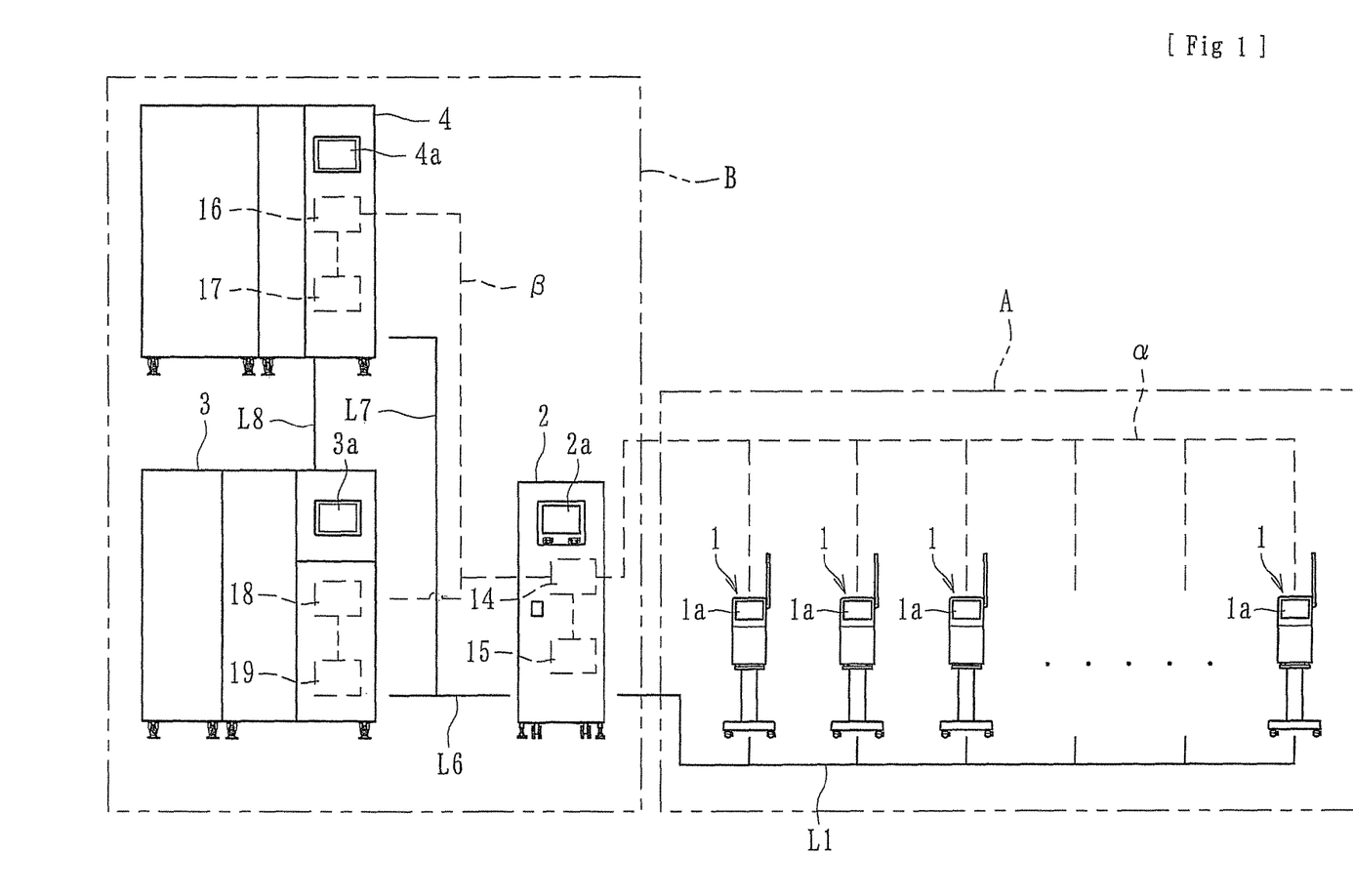
FIG. 1 is an overall schematic view of a blood purification system.

A blood purification system according to the present embodiment produces a dialysate with a predetermined concentration using an undiluted dialysate. The blood purification system supplies the dialysate to a plurality of dialysis monitors. As illustrated in FIG. 1, the blood purification system is mainly configured to include a plurality of monitoring devices 1 installed in a dialysis room A (treatment room) in a medical field such as a hospital. A dialysate supplying device 2 is installed in a machine room B. The machine room B is a place separated from the dialysis room A in the medical field or hospital. A dissolving device 3 and a water treatment device 4 may be included in the machine room B.

The monitoring device 1 (blood purification mechanism) is attached to a dialyzer 5 (blood purifier) in order to perform a blood purification treatment (hemodialysis treatment) on a patient. The monitoring device 1 supplies the dialysate supplied from the dialysate supplying device 2 to the dialyzer 5. A plurality of monitoring devices 1 is installed at the dialysis room A. In the monitoring devices 1, touch panels is are arranged that can perform an instruction and a predetermined display of the hemodialysis treatment or other control content (cleaning or disinfecting).

Figure 2:
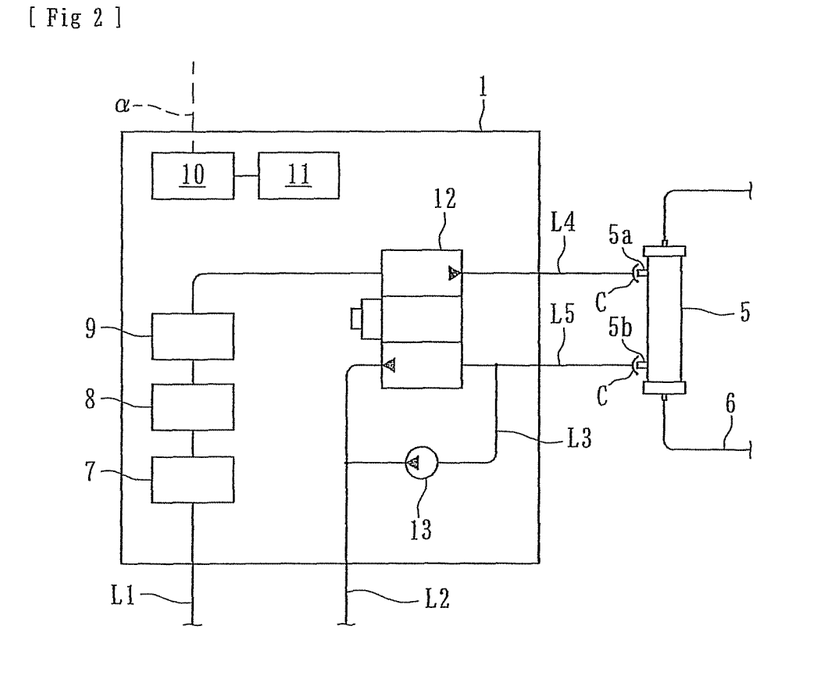
FIG. 2 is a schematic view of a configuration of a monitoring device in the blood purification system.

More specifically, as illustrated in FIG. 2, a pipe L1, extending from the dialysate supplying device 2, is drawn into each of the plurality of monitoring devices 1 installed at the dialysis room A. A pipe L2 is connected to a liquid discharge device (not illustrated). A duplex pump 12 is arranged across the pipes L1 and L2. Out of the pipes L1 and L2, in the pipe L1, a flow rate detection sensor 7, a liquid pressure protection sensor 8 and a conductivity detection sensor 9 are arranged inside the monitoring device 1. The flow rate detection sensor 7 detects a flow rate of a liquid flowing in the pipe L1. The liquid pressure detection sensor 8 detects a liquid supply pressure of the liquid. The conductivity detection sensor 9 detects conductivity (concentration) of the liquid.

In addition, a dialysate introduction line L4, communicating with the pipe L1, and a dialysate discharge line L5, communicating with the pipe L2, extend from the duplex pump 12. A tip of the dialysate introduction line L4 can be connected to a dialysate introduction port 5a of the dialyzer 5 via a coupler C. A tip of the dialysate discharge line L5 can be connected to a dialysate discharge port 5b of the dialyzer 5 via the coupler C. In this manner, the dialyzer 5, depending on each patient is attached to each monitoring device 1. A blood circuit 6, connected to the dialyzer 5, performs extracorporeal circulation on the patients' blood.

A pump room of the duplex pump 12 is divided into a liquid supply side pump room, connected to the pipe L1, and a discharge side pump room, connected to the pipe L2 by a single plunger (not illustrated). The plunger performs reciprocation in the pump room. It supplies the dialysate or a cleaning solution. The cleaning solution is supplied to the liquid supply side pump room and to the dialyzer 5. Then, the dialysate inside the dialyzer 5 is sucked into the discharge side pump room. Further, a pipe L3 is formed inside the monitoring device 1, the pipe L3 bypasses the duplex pump 12 and communicates with the pipe L2 and the dialysate discharge line L5. A water removal pump 13 is arranged in the middle of the pipe L3. It is possible to perform water removal on the patient's blood that flows inside the dialyzer 5 by driving the water removal pump 13.

Instead of the duplex pump 12, a so-called chamber type pump may be used. Sensors, such as the flow rate detection sensor 7, the liquid pressure detection sensor 8 or the conductivity detection sensor 9, or other generic sensors may be added or may be arranged in the pile L1. Further, in the present embodiment, the sensors are arranged in the pipe L1. However, they may be arranged in the other pipe (for example, the pipe L2). For example, the sensors, the flow rate detection sensor 7, the liquid pressure detection sensor 8 or the conductivity detection sensor 9, may be arranged in any one of the pipe L1 and the pipe L2, or may be arranged in both pipes.

The water treatment device 4 includes a module (purifying filter) having an inherent filtration membrane. It obtains clean water (RO water) by purifying raw water. The water treatment device 4 is configured to be capable of supplying the clean water to the dissolving device 3. It is connected to the dissolving device 3, via a pipe L8. The water treatment device 4 is capable of supplying the clean water to the dialysate supplying device 2 by being connected to the dialysate supplying device 2 via pipes L6 and L7. The clean water obtained by the water treatment device 4 is used when the dialysate supplying device 2 produces the dialysate. Also, the water treatment device 4 is used as the cleaning water for cleaning the pipes of the dialysate supplying device 2 or the monitoring devices 1. The configuration may also be made such that the water treatment device 4, supplying clean water, is connected to a personal dialysis device (not illustrated) or a dissolving device, that dissolves a powdered dialysis drug.

In addition, the water treatment device 4 includes a touch panel 4a and interface unit 16 and a control unit 17. The touch panel 24a can perform an instruction and display control content relating to the water treatment. The interface unit 16 is electrically connected to a LAN cable β. If the interface unit 16 receives predetermined information from the dialysate supplying device 2, a predetermined operation (producing the clean water) is performed by the control unit 17 based on the information.

For example, a predetermined amount of powder drug for dialysis is dispensed into the dissolving device 3. The dissolving device mixes the powder drug, for dialysis, with the clean water supplied from the water treatment device 4. It produces the undiluted dialysate with a predetermined concentration. The dissolving device 3 includes a touch panel 3a, an interface unit 18 and a control unit 19. The touch panel 3a can perform an instruction and a display control content relating to the producing of the undiluted dialysate. The interface unit 18 is electrically connected to a LAN cable β (to be described later). If the interface unit 18 receives predetermined information from the dialysate supplying device 2, a predetermined operation (producing the undiluted dialysate) is performed by the control unit 19, based on the information. The dissolving device 3 is connected to the dialysate supplying device 2, via the pipe L6. The dissolving device 3 is configured to supply the produced undiluted dialysate to the dialysate supplying device 2.

The dialysate supplying device 2, the dissolving device 3 and the water treatment device 4 are connected to each other on a local area network (LAN). This enables bilateral information communication. The LAN is not limited to use of the LAN cable β (wired) as in the present embodiment, but may be any one which enables the bilateral information communication in a wireless manner (wireless LAN). Instead of the LAN, a system may be used that transmits an electrical signal (process signal) unilaterally from the dialysate supplying device 2 to the dissolving device 3 and the water treatment device 4.

The dialysate supplying device 2 (supplying mechanism) can produce the dialysate with a predetermined concentration by using the clean water obtained from the water treatment device 4 and the undiluted dialysate produced by the dissolving device 3. The dialysate supplying device 2 supplies the produced dialysate to each of the monitoring devices 1 (blood purification mechanisms). The dialysate supplying device 2 is connected to each of the plurality of monitoring devices 1, via the pipe L1. The dialysate supplying device 2 is configured to supply a desired liquid such as the dialysate, the cleaning water and the antiseptic solution to each of the monitoring devices 1, via the pipe L1. The dialysate supplying device 2 includes a touch panel 2a that can perform an instruction and display control content relating to the supplying of the dialysate, the cleaning or the disinfecting.

Here, in the blood purification system according to the present embodiment, the dialysate supplying device 2 (supplying mechanism) and each of the monitoring devices 1 (blood purification mechanisms) are connected to each other on the local area network (LAN). This enables the bilateral information communication. In this configuration of the blood purification system, the predetermined individual information relating to the plurality of monitoring devices 1 can be transmitted from each of the monitoring devices 1 to the dialysate supplying device 2.

LAN connection is made via the LAN cable α between the dialysate supplying device 2 and each of the monitoring devices 1. The dialysate supplying device 2 includes the interface unit 14 and the control unit 15 in order to communicate with the monitoring devices 1, via the LAN cable α. Each of the monitoring devices 1 includes the interface unit 10 and the control unit 11 (refer to FIG. 2) in order to communicate with the dialysate supplying device 2 via the LAN cable α. The LAN is not limited to use of the LAN cable α (wired) as in the present embodiment. A connection may be used that enables the bilateral information communication wirelessly (wireless LAN).

Further, in the dialysate supplying device 2, the interface unit 14 receives the predetermined information from the monitoring devices 1. The predetermined operation (producing the dialysate) is performed by the control unit 15 based on the information. The predetermined information can be transmitted to the monitoring devices 1 via the interface unit 14. In addition, in the monitoring devices 1, the interface unit 10 receives the predetermined information from the dialysate supplying device 2. The predetermined operation (priming before treatment, hemodialysis treatment, re-transfusion, cleaning and disinfecting) is performed by the control unit 11 based on the information. The predetermined information can be transmitted to the dialysate supplying device 2, via the interface unit 10.

In particular, the predetermined individual information relating to the plurality of monitoring devices 1, which is to be transmitted to the dialysate supplying device 2, includes, for example, information relating to a temperature, a pressure, concentration, a flow rate or time (liquid supply time and operation time, or the like) of a liquid (dialysate, cleaning water, or the like) flowing inside the monitoring devices 1. The information is supplied from the dialysate supplying device 2 to the monitoring devices 1 (parameter information), or information (process information) relating to a process performed by the monitoring devices 1 (priming process before treatment, hemodialysis treatment process, re-transfusion process, cleaning and disinfecting process, substitution process, or the like). The substitution process means a process where a sufficient amount of dialysate is circulated into the pipe to complete the cleaning and disinfecting process and where the inside of the pipe is completely filled with the dialysate before a starting treatment. In this case, a substitution solution indicates the dialysate.

In addition, in the present embodiment, in addition to the real-time information described above, setting information that is preset in each of the monitoring devices 1 can be transmitted from each of the monitoring devices 1 to the dialysate supplying device 2. Preset setting information may include separating dimension from the dialysate supplying device 2 to the monitoring devices 1, flow rate or pipe capacity in cleaning water, antiseptic solution or substitution solution, which is required when performing cleaning, disinfecting or substitution, and frequency of cleaning and disinfecting to be performed.

Here, in the present embodiment, under a condition where predetermined information is transmitted from the monitoring devices 1, a predetermined operation is performed by the dialysate supplying device 2. In this manner, under a condition where predetermined information is transmitted from the monitoring devices 1, a predetermined operation is performed by the dialysate supplying device 2. Therefore, various operations can be performed by giving priority to a condition of the monitoring devices 1, thereby further improving operation.

Thus, under a condition where the predetermined information is transmitted from the monitoring devices 1, assuming a configuration where a predetermined operation is performed by the dialysate supplying device 2, for example, the predetermined information may be requirement information or permission information that requires or permits the cleaning, the disinfecting or the substitution of the pipe in the monitoring devices 1. In this case, since the predetermined information is the requirement information or the permission information that requires or permits cleaning, disinfecting, or substitution of the pipe in the blood purification mechanism, it is possible to further improve the operation during cleaning, disinfecting or substitution. Hereinafter, control content in the dialysate supplying device 2, in this case, will be described with reference to the flowchart in FIG. 3.

Figure 3:
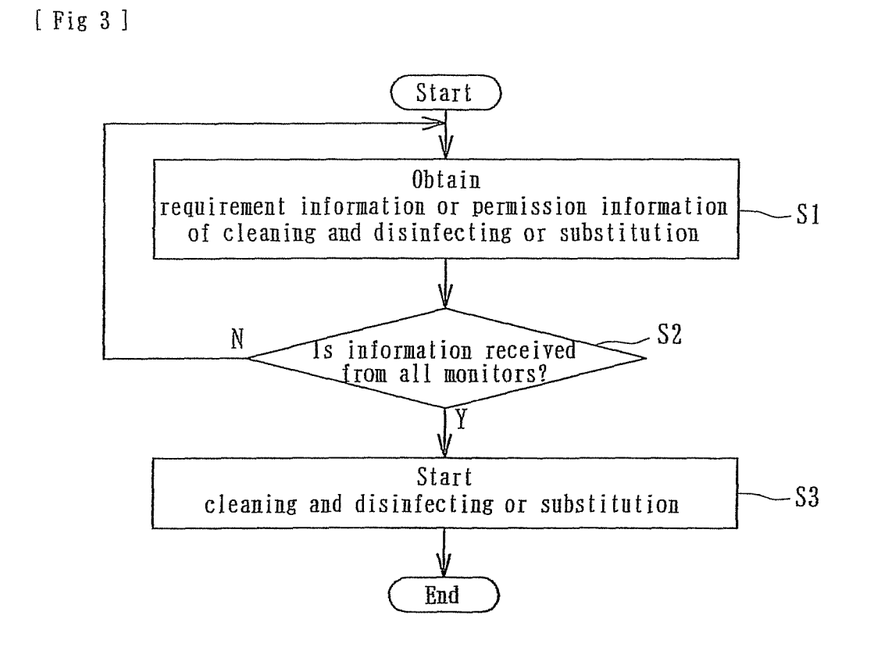
FIG. 3 is a flowchart of control content (priority control) of a dialysate supplying device in the blood purification system.

For example, after transmitting it to each of the monitoring devices 1 whether or not there is the requirement information or the permission information of the cleaning, the disinfecting or the substitution, the requirement information or the permission information of the cleaning, the disinfecting or the substitution is obtained from each of the monitoring devices 1 (S1). Then, it is determined whether or not the requirement information or the permission information of the cleaning and the disinfecting is received from all the monitoring devices 1 (S2). If it is determined that the requirement information or the permission information of the cleaning and the disinfecting is received from all the monitoring devices 1, the step proceeds to S3. Thus, the cleaning and the disinfecting start.

In addition, in the present embodiment, information relating to an amount of dialysate to be used in each of the monitoring devices 1 is transmitted from the monitoring devices 1 to the dialysate supplying device 2. In this manner, the information relating to an amount of dialysate to be used in each of the monitoring devices 1 is transmitted from the monitoring devices 1 to the dialysate supplying device 2. Thus, the actual condition of the monitoring devices 1 can be accurately determined. The dialysate supplying device 2 can supply the dialysate or the undiluted dialysate.

The information relating to an amount of dialysate to be used in each of the monitoring devices 1 is transmitted from the monitoring devices 1 to the dialysate supplying device 2. The dialysate supplying device 2 may be configured, for example, to produce the dialysate or the undiluted dialysate, to instruct the producing, or to send the notification to prompt the producing, based on the amount of the dialysate to be used that is transmitted from the monitoring devices 1. In this case, the dialysate supplying device 2 produces the dialysate or the undiluted dialysate, instructs the producing, or sends the notification to prompt the producing, based on the amount of the dialysate to be used which is transmitted from the monitoring devices 1. Therefore, it is possible to produce a more appropriate amount of the dialysate or the undiluted dialysate. Hereinafter, control content in the dialysate supplying device 2 in this case will be described with reference to the flowchart in FIG. 4.

Figure 4:
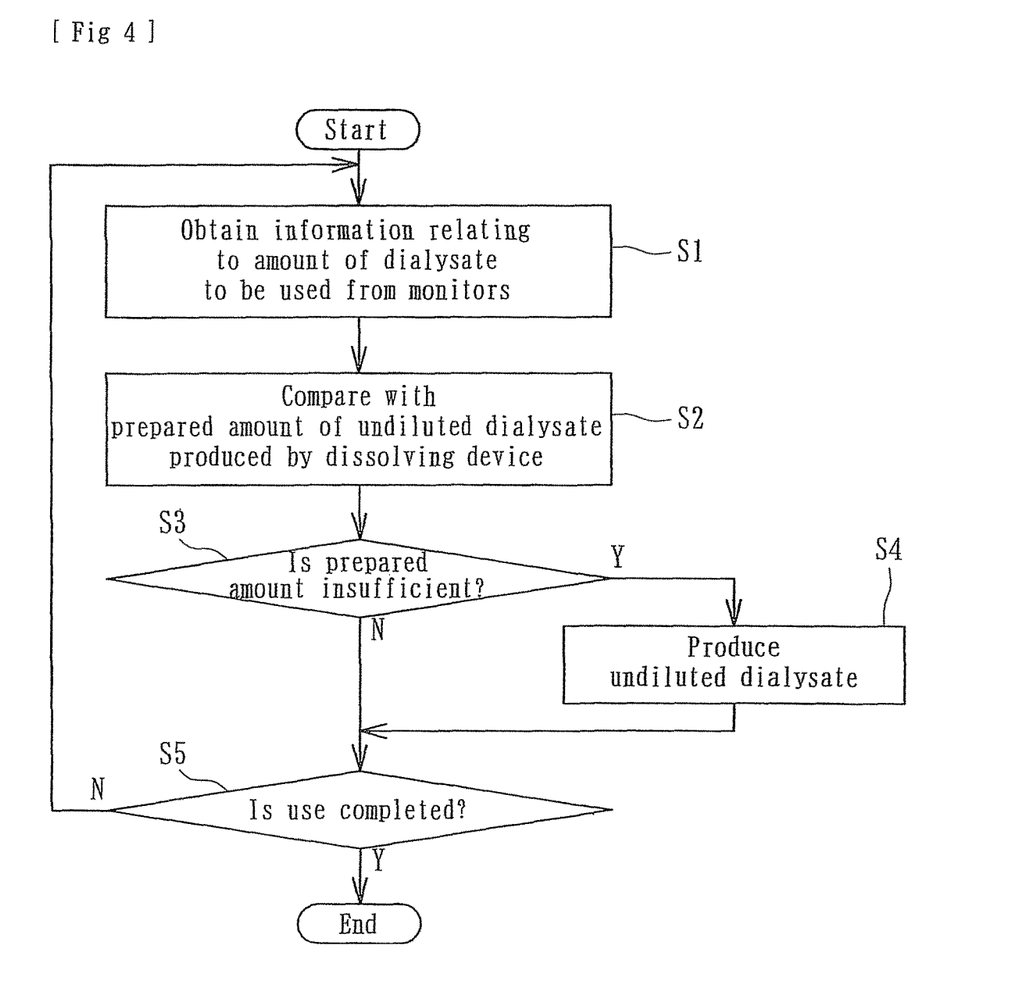
FIG. 4 is a flowchart of control content (producing an undiluted dialysate) of the dialysate supplying device in the blood purification system.

For example, after instructing each of the monitoring devices 1 to transmit the information relating to the amount of the dialysate to be used, the information relating to the amount of the dialysate to be used (for example, information on the amount, the flow rate, the supply duration, and the supply time of the dialysate) is obtained from each of the monitoring devices 1 (S1). Without instructing each of the monitoring devices 1 to transmit the information relating to the amount of the dialysate to be used, the information relating to the amount of the dialysate to be used may be transmitted and obtained from each of the monitoring devices 1. Then, based upon the information relating to the amount of the dialysate to be used, which is received from each of the monitoring devices 1, the amount of the dialysate to be used in all the monitoring devices 1 is determined. The amount of the dialysate to be used is compared with a prepared amount of the undiluted dialysate produced by the dissolving device 3 (S2).

The comparison in S2 determines whether or not the prepared amount of the undiluted dialysate produced by the dissolving device 3 is insufficient (S3). If the prepared amount of the undiluted dialysate is determined to be insufficient, an instruction is transmitted to the dissolving device 3 and the water treatment device 4. The undiluted dialysate is produced by an amount corresponding to the insufficient amount (S4). Thereafter, it is determined whether or not use of the dialysate (use thereof during the dialysis treatment or when the dialysate is used for the priming or the re-transfusion) is completed (S5). If the use is determined to be completed, a series of controls is completed. If in S3, it is determined that the prepared amount of the undiluted dialysate is sufficient, the step proceeds to S5 without performing the process in S4. Here, when using a dissolving device or a water treatment device which is not interlocked, it is possible to perform a notification to prompt the producing of the dialysate or the undiluted dialysate.

Further, in the present embodiment, the information relating to the amount of the cleaning water or the amount of the antiseptic solution (dialysate) required for each of the monitoring devices 1 is transmitted from the monitoring devices 1 to the dialysate supplying device 2. In this manner, the information relating to the required amount of the cleaning water or the required amount of the antiseptic solution for each of the monitoring devices 1 is transmitted from the monitoring devices 1 to the dialysate supplying device 2. Therefore, the actual condition of the monitoring devices 1 can be accurately determined. Thus, the dialysate supplying device 2 can supply the cleaning water or the antiseptic solution.

The information relating to the required amount of the cleaning water, the antiseptic solution or the substitution solution (the dialysate) for each of the monitoring devices 1 is transmitted from the monitoring devices 1 to the dialysate supplying device 2. The dialysate supplying device 2 may be configured, for example, to supply the cleaning water, the antiseptic solution, or the substitution solution based on the required amount of the cleaning water, the required amount of the antiseptic solution or the required amount of the substitution solution that is transmitted from the monitoring devices 1. In this case, the dialysate supplying device 2 supplies the cleaning water, the antiseptic solution or the substitution solution based on the required amount of the cleaning water, the required amount of the antiseptic solution or the required amount of the substitution solution that is transmitted from the monitoring devices 1. Therefore, it is possible to produce a more appropriate amount of the cleaning water, the antiseptic solution or the substitution solution.

The cleaning and the disinfecting are performed by an automatic operation during a time zone when no hemodialysis treatment is performed. Progress information of the cleaning, the disinfecting and the substitution, which are performed by the monitoring devices 1, may be transmitted to the dialysate supplying device 2 in real-time. Thus, the time for the cleaning, the disinfecting and the substitution may be automatically extended according to the progress. Hereinafter, control content in the dialysate supplying device 2 in this case will be described with reference to the flowchart in FIG. 5.

Figure 5:
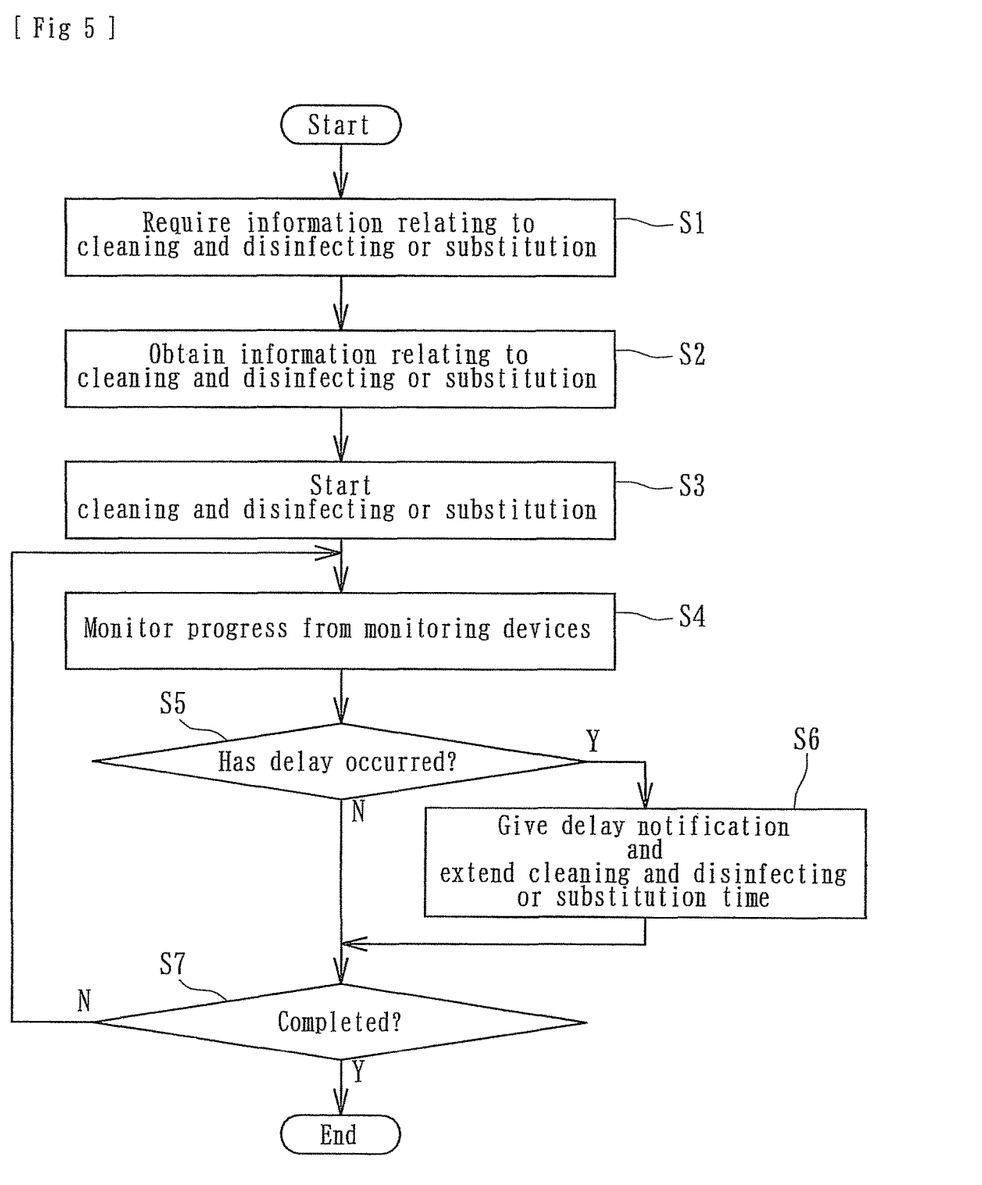
FIG. 5 is a flowchart of control content (cleaning and disinfecting time extension) of the dialysate supplying device in the blood purification system.

The information relating to the cleaning and disinfecting or the substitution (for example, type, amount, flow rate, supply duration, and supply time of the liquid, or temperature or concentration of the liquid) is required by each of the monitoring devices 1 (S1). In this manner, after the information relating to the cleaning and disinfecting or the substitution is obtained from each of the monitoring devices 1 (S2), the cleaning and disinfecting or the substitution starts (S3). Then, the information from the monitoring devices 1 is obtained in real-time. The progress of the cleaning and disinfecting or the substitution is monitored (S4). Then, it is determined whether or not a delay occurs in the cleaning and disinfecting or the substitution (S5).

In S5, if it is determined that the delay has occurred in the cleaning and disinfecting or the substitution, the step proceeds to S6. The delay notification is given, and the cleaning and disinfecting time or the substitution time is extended according to the delay time. Thereafter, it is determined whether or not the cleaning or the substitution and disinfecting are completed (S7). If determined to be completed, a series of controls is completed. If in S5, it is determined that the delay has not occurred, the step proceeds to S7 without performing the process in S6.

Here, the history of the cleaning and disinfecting or the substitution (for example, history such as a notification that the cleaning, the disinfecting or the substitution has been satisfactorily performed, and a notification that a malfunction has occurred) is displayed on the touch panel is in each of the monitoring devices 1. The history relating to the cleaning, the disinfecting or the substitution in each of the monitoring devices 1 is displayed (batch display or selective display) on the touch panel 2a in the dialysate supplying device 2. In this manner, the dialysate supplying device 2 can display the history relating to the cleaning, the disinfecting or the substitution in each of the monitoring devices 1. Therefore, it is possible to determine overall confirmation as to whether or not the cleaning, the disinfecting or the substitution of each of the monitoring devices 1 has been satisfactorily performed. Thus, compared to a case where visually and respectively confirming the history displayed on each of the monitoring devices 1, it is possible to improve workability. When the cleaning, the disinfecting or the substitution is insufficient, it is preferable to configure the device so as to give such a notification to that effect.

Furthermore, in the present embodiment, the dialysate supplying device 2 can detect an abnormality by comparing the information of the liquid supplied to the monitoring devices 1 with the predetermined information transmitted from the monitoring devices 1. In this manner, the dialysate supplying device 2 can detect the abnormality by comparing the information of the liquid supplied to the monitoring devices 1 with the predetermined information transmitted from the monitoring devices 1. Therefore, more precise self-diagnosis can be performed. Also, reliability of the blood purification system can be further improved. Thus, it is possible to eliminate a need for an individual sensor for the self-diagnosis. Hereinafter, control content to detect the abnormality will be described with reference to the flowcharts in FIGS. 6 to 8.

Figure 6:
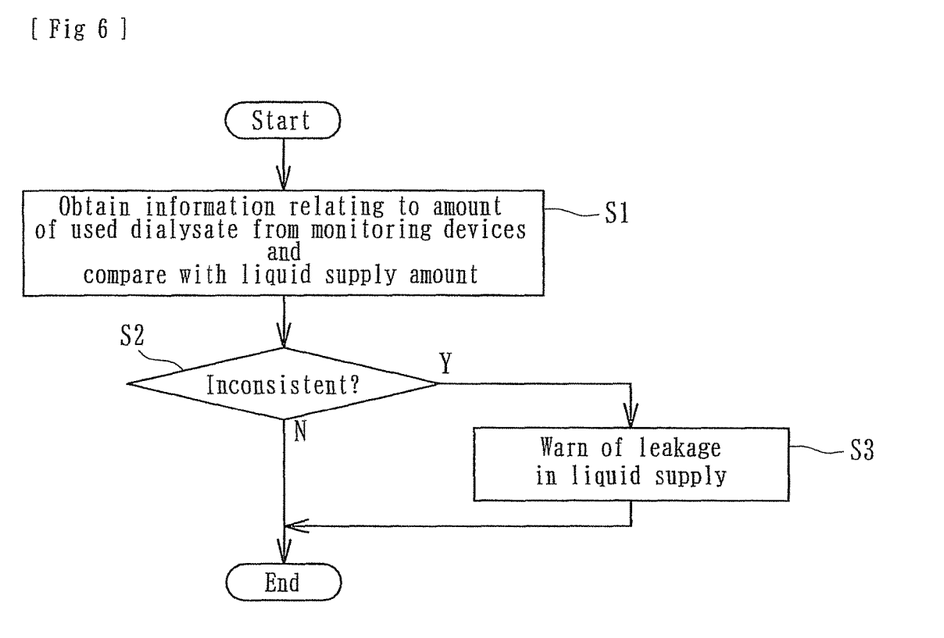
FIG. 6 is a flowchart of control content (self-diagnosis of leakage in liquid supply) of the dialysate supplying device in the blood purification system.

First, the self-diagnosis of leakage in the liquid supply will be described with reference to the flowchart in FIG. 6.

The amount of the dialysate (flow rate of the dialysate) used in each of the monitoring devices 1 is detected by the flow rate detection sensor 7. The detection information is transmitted to the dialysate supplying device 2. In this manner, information is obtained on the amount of the dialysate used from the monitoring devices 1. The amount of the dialysate used in the monitoring devices 1 is compared with the liquid supply amount of the dialysate supplied from the dialysate supplying device 2 (S1). Then, in S2, if it is determined that the amount of the dialysate used in the monitoring devices 1 and the liquid supply amount of the dialysate supplied from the dialysate supplying device 2 do not match and are inconsistent with each other, it is determined that there is leakage of the liquid supply in the pipe that circulates the dialysate. Then, a warning indicating that effect is issued (S3). In S2, if it is determined that the amount of the dialysate used in the monitoring devices 1 matches the liquid supply amount of the dialysate supplied from the dialysate supplying device 2, the self-diagnosis is completed as it is without performing the warning of S3. In S1, the flow rate detection sensor 7 detects the amount of the dialysate (flow rate of the dialysate) used in each of the monitoring devices 1. However, for example, it may be configured to compare the liquid supply amount of the dialysate supplied from the dialysate supplying device 2 by using a setting value (theoretical value obtained from the capacity of the pipe in the monitoring devices 1) of the amount of the dialysate to be used in each of the monitoring devices 1.

Figure 7:
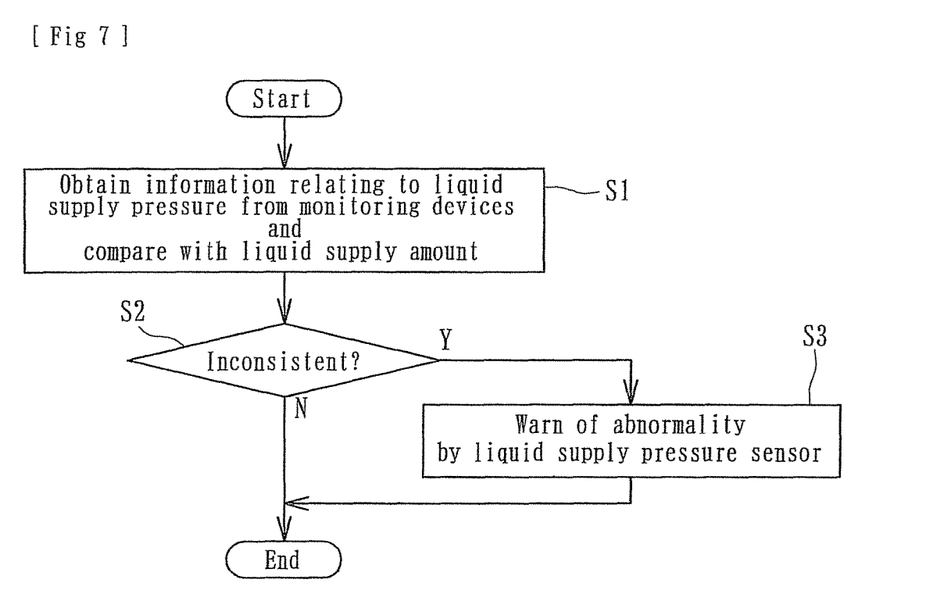
FIG. 7 is a flowchart of control content (self-diagnosis of an abnormality in a liquid supply pressure sensor) of the dialysate supplying device in the blood purification system.

Next, the self-diagnosis of the liquid pressure detection sensor 8 will be described with reference to the flowchart in FIG. 7.

The liquid pressure (liquid supply pressure) of the dialysate supplied to each of the monitoring devices 1 is detected by the liquid pressure detection sensor 8. The detection information is transmitted to the dialysate supplying device 2. In this manner, the detection information is obtained by the liquid pressure detection sensor 8. The detection information is compared with the liquid supply pressure of the dialysate supplied from the dialysate supplying device 2 (S1). S2 determines if the detection information obtained by the liquid pressure detection sensor 8 and the liquid supply pressure detected in the dialysate supplying device 2 sides do not match and are inconsistent with each other. The liquid pressure detection sensor 8 determines that an abnormality has occurred due to a failure. Then, a warning to that effect is performed (S3). In S2, if it is determined that the detection information obtained by the liquid pressure detection sensor 8 matches the liquid supply pressure detected in the dialysate supplying device 2 side, the self-diagnosis is completed without performing the warning of S3.

Figure 8:
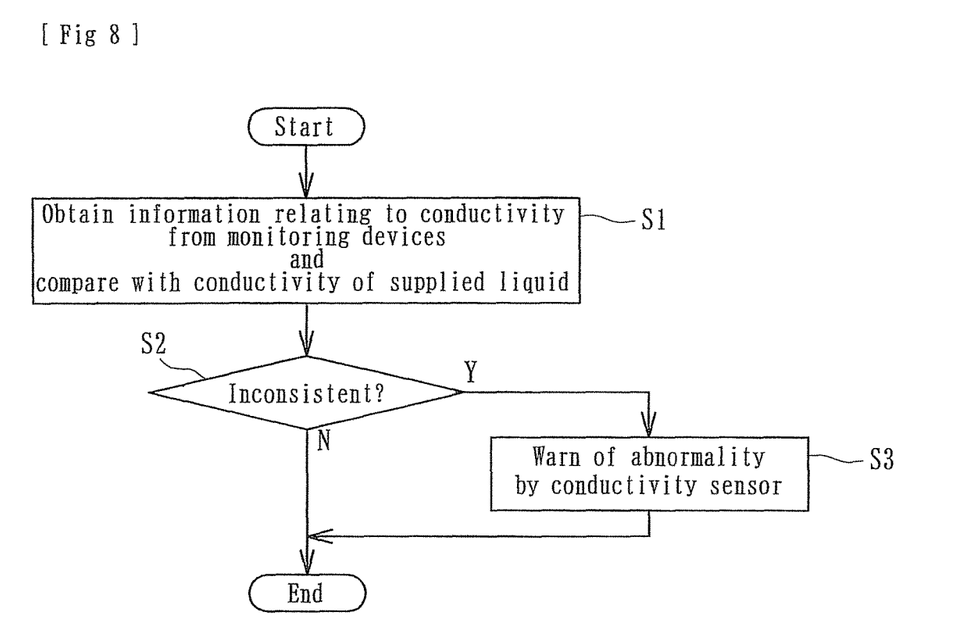
FIG. 8 is a flowchart of control content (self-diagnosis of an abnormality in a conductivity sensor) of the dialysate supplying device in the blood purification system.

Next, the self-diagnosis of the concentration of the dialysate will be described with reference to the flowchart in FIG. 8.

The concentration (conductivity) of the dialysate supplied to each of the monitoring devices 1 is detected by the conductivity detection sensor 9. The detection information is transmitted to the dialysate supplying device 2. In this manner, the concentration information of the dialysate in the monitoring devices 1 is obtained. The detection information is compared with the concentration (conductivity) of the dialysate supplied from the dialysate supplying device 2 (S1). In S2, it is determined if the detection information detected by the conductivity detection sensor 9 and the concentration (conductivity) detected in the dialysate supplying device 2 side do not match and are inconsistent with each other. The conductivity detection sensor 9 determines that an abnormality has occurred due to a failure. A warning to that effect is performed (S3). In S2, if it is determined that the detection information detected by the conductivity detection sensor 9 matches the concentration (conductivity)

detected in the dialysate supplying device 2 side, the self-diagnosis is completed. It is performed without the warning of S3.

According to the above-described embodiment, the predetermined individual information relating to the plurality of monitoring devices 1 (blood purification mechanisms) can be transmitted from each of the monitoring devices 1 to the dialysate supplying device 2 (supplying mechanism). Therefore, the actual condition of the monitoring devices 1 can be accurately determined. The dialysate supplying device 2 performs an operation. In particular, the predetermined information to be transmitted includes information relating to a temperature, a pressure, a concentration, a flow rate, or time of the liquid supplied from the dialysate supplying device 2 to the monitoring devices 1. Therefore, real-time information in the monitoring devices 1 can be transmitted to the dialysate supplying device 2. Thus, the actual condition of the monitoring devices 1 can be more accurately determined.

Furthermore, according to the present embodiment, the supplying mechanism includes the dialysate supplying device 2. The dialysate supplying device 2 produces the dialysate with the predetermined concentration by using the clean water and the undiluted dialysate. The blood purification mechanism includes the monitoring devices 1. The monitoring devices 1 supply the dialysate supplied from the dialysate supplying device 2 to the dialyzer 5 (blood purifier). Therefore, the blood purification system can be applied to a central system. In addition, the dialysate supplying device 2 and the monitoring devices 1 can bilaterally communicate with each other. Thus, various items of the information can be communicated between the dialysate supplying device 2 and the monitoring devices 1. Accordingly, it is possible to perform a more appropriate and operable blood purification treatment.

Figure 9:
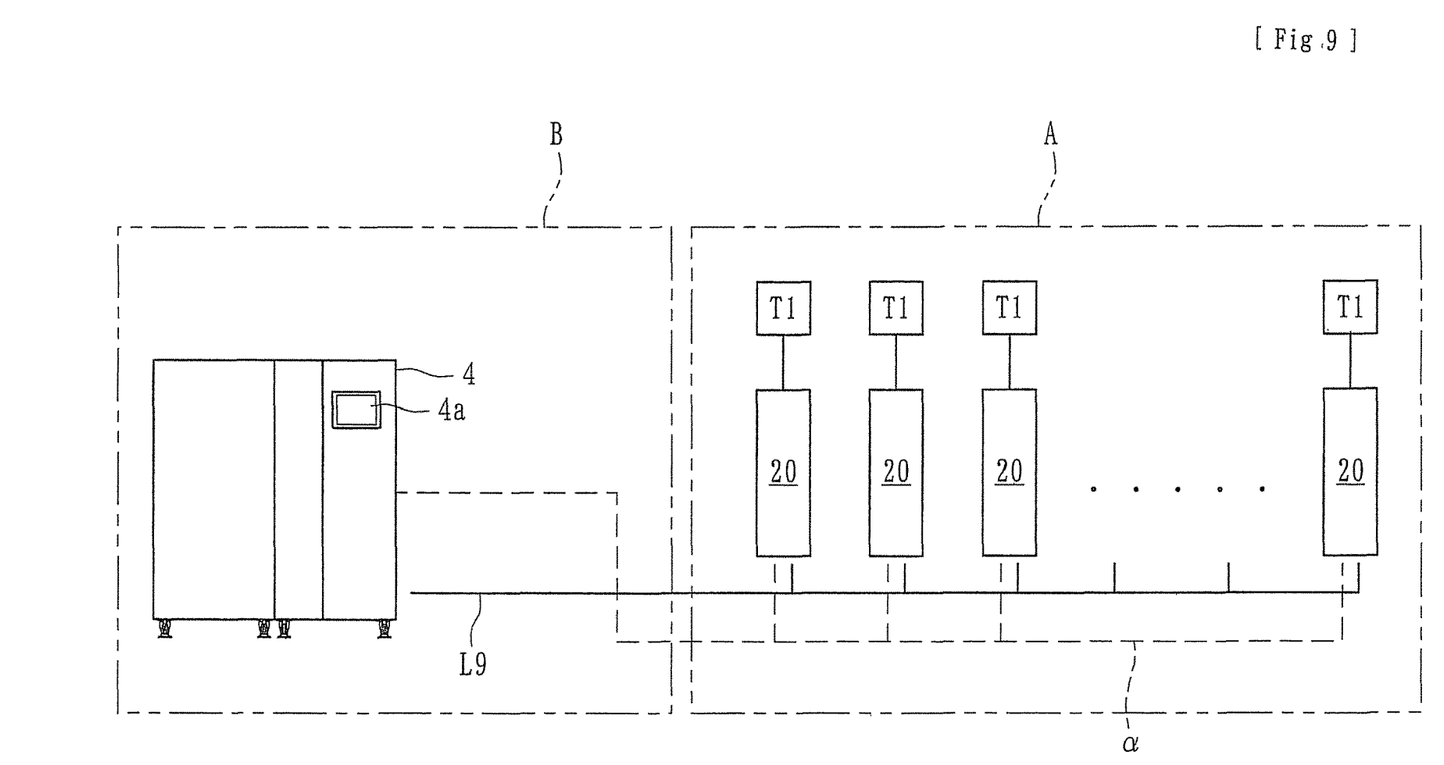
FIG. 9 is an overall schematic view of a blood purification system according to another embodiment.

The blood purification system according to the present embodiment has been described, but the present disclosure is not limited. For example, instead of those adapted to have the central system as described above, as illustrated in FIG. 9, the blood purification system may be applied to a system where the supplying mechanism includes the water treatment device 4. The water treatment device 4 produces the clean water. The blood purification system includes the personal dialysis devices 20 that produces the dialysate with the predetermined concentration by using the clean water supplied from the water treatment device 4 and supply the dialysate to the dialyzer 5 (blood purifier). In this case, the personal dialysis devices 20 include tanks T1, respectively, containing the undiluted dialysate or the antiseptic solution. The tanks T1 are connected to the water treatment device 4 by a pipe L9. The personal dialysis devices 20 can produce the dialysate with the predetermined concentration by using the clean water supplied from the water treatment device 4 and the undiluted dialysate inside the tanks T1, or can produce the diluted antiseptic solution.

In the embodiment illustrated in FIG. 1, the supplying mechanism includes the dialysate supplying device 2 (including the dissolving device 3 and the water treatment device 4) that supplies the dialysate to each of the monitoring devices 1. However, the blood purification system may be configured such that the blood purification mechanism has the dialyzer 5 (blood purifier) and the personal dialysis device 20. The personal dialysis device 20 produces the dialysate from the undiluted dialysate inside the tanks T1.

Figure 10:
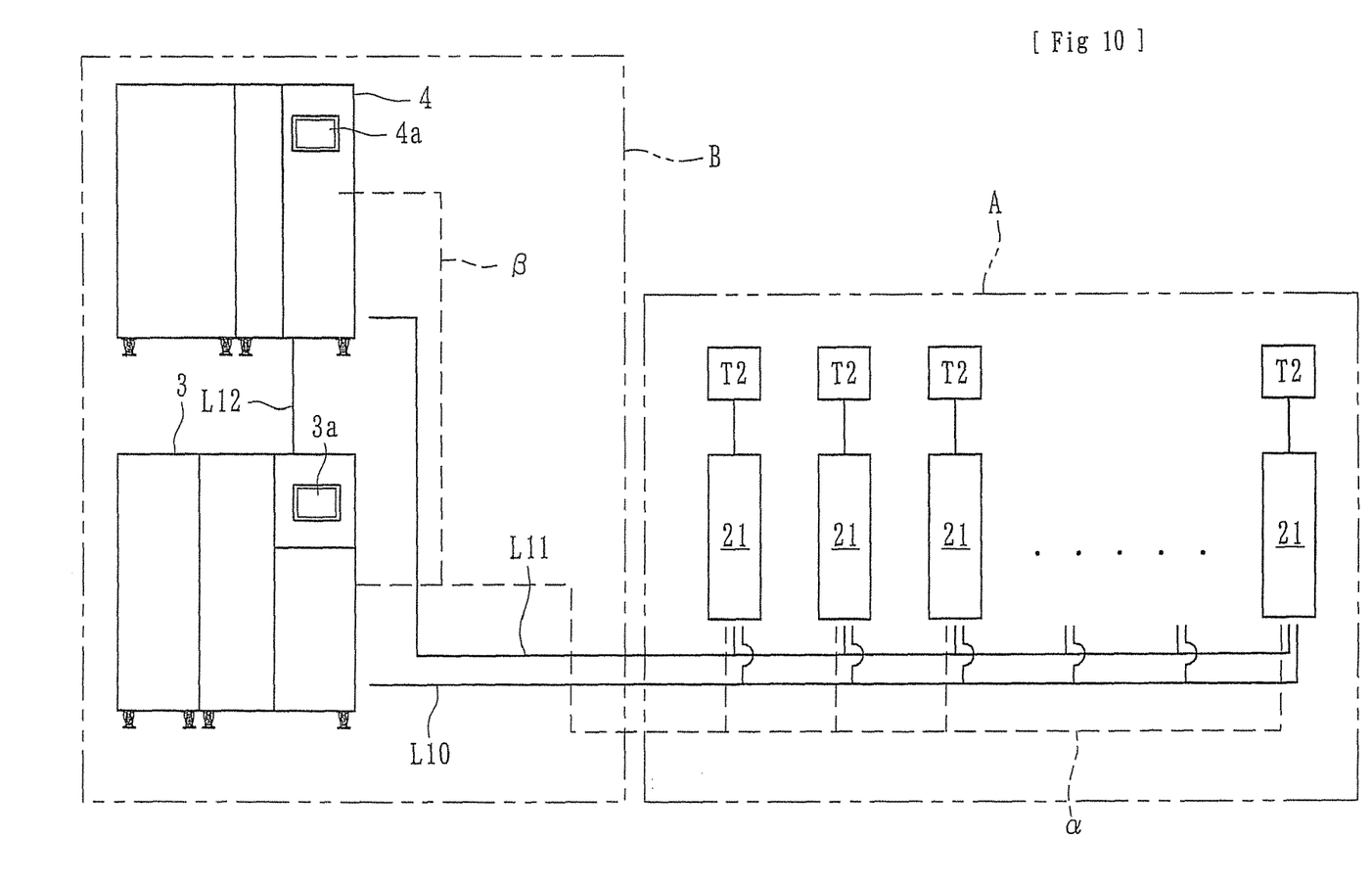
FIG. 10 is an overall schematic view of a blood purification system according to a further embodiment.

Furthermore, for example, instead of those adapted to have the central system, as illustrated in FIG. 10, the blood purification system may be applied to a system where the supplying mechanism includes the water treatment device 4 and the dissolving device 3. The water treatment device 4 produces the cleaning water. The dissolving device 3 produces the undiluted dialysate with the predetermined concentration by using the clean water produced by the water treatment device 4. The blood purification mechanism includes personal dialysis devices 21. The personal dialysis devices 21 produce the dialysate with the predetermined concentration by using the undiluted dialysate and the clean water, respectively, supplied from the dissolving device 3 and the water treatment device 4. The personal dialysis devices 21 supply the dialysate to the dialyzer 5 (blood purifier). In this case, the personal dialysis devices 21 include tanks T2, respectively, that contains the antiseptic solution. The tanks T2 are connected to the dissolving device 3 and the water treatment device 4 by pipes L10 and L11. The personal dialysis devices 21 produce the dialysate with the predetermined concentration by using the undiluted dialysate and the clean water. The undiluted dialysate and clean water are, respectively, supplied from the dissolving device 3 and the water treatment device 4. The personal dialysis devices 21 also may produce the diluted antiseptic solution.

In the embodiment illustrated in FIG. 1, the supplying mechanism includes the dialysate supplying device 2 including the dissolving device 3 and the water treatment device 4. The supplying mechanism supplies the dialysate to each of the monitoring devices 1. However, the blood purification system may include the blood purification mechanism with the dialyzer 5 (blood purifier) and the personal dialysis devices 21. The personal dialysis devices 21 produce the dialysate by using the undiluted dialysate and the clean water that are supplied from the supplying mechanism side.

In addition, in the present embodiment, the LAN connection is made to enable bilateral communication between the dialysate supplying device 2 and the monitoring devices 1. However, it is sufficient if the predetermined individual information relating to the plurality of monitoring devices 1 (blood purification mechanism) can be transmitted from each of the monitoring devices 1 to the dialysate supplying device 2. The predetermined information may also be unilaterally transmitted from the monitoring devices 1 to the dialysate supplying device 2. The present embodiment is applied to a system to perform the hemodialysis treatment. Additionally, the present embodiment may be applied to a blood purification system to perform a different blood purification treatment.

As long as a blood purification system is configured so that predetermined individual information relating to multiple blood purification mechanisms can be transmitted from each of the blood purification mechanisms to a supplying device, the blood purification system can be applied to a device having other added functions.

The present disclosure has been described with reference to the preferred embodiment. Obviously, modifications and alternations will occur to those of ordinary skill in the art upon reading and understanding the preceding detailed description. It is intended that the present disclosure be construed to include all such alternations and modifications insofar as they come within the scope of the appended claims or their equivalents.

What is claimed is:
1. A blood purification system comprising:
multiple blood purification mechanisms including a blood purifier performing a blood purification treatment on a specific patient; and a supplying mechanism including a device for receiving signals from each of the blood purification mechanisms, each blood purification mechanism provides a specific signal, the supply mechanism programmed to supply a dialysate, an undiluted dialysate, clean water or an antiseptic solution, each of the blood purification mechanisms receives its specific supply of the dialysate, undiluted dialysate, clear water or antiseptic solution in response to its specific received signal;

each multiple blood purification mechanism comprising a monitoring device or personal dialysis device programmed for sending the specific signals, the monitoring device or personal dialysis device sending the specific signals to the supply mechanism relating to the specific information including temperature, a pressure, a concentration, a flow rate, or time of a liquid that is supplied from the supplying mechanism to the blood purification mechanisms, the monitoring device or personal dialysis device enabling bilateral information communication between each of the blood purification mechanism and the supplying mechanism so that information is received from all of the blood purification mechanisms;

the supplying mechanism obtains requirement information or permission information that enables cleaning, disinfecting or the substitution of a pipe in the specific blood purification mechanism from each of the blood purification mechanisms and the cleaning, disinfecting or the substitution of the pipe in the specific blood purification mechanism is started on a condition that the specific information is received from all of the blood purification mechanisms.

2. The blood purification system according to claim 1, wherein the supplying mechanism includes a dialysate supplying device that produces a dialysate with a predetermined concentration by using clean water and an undiluted dialysate; and the blood purification mechanism includes the monitoring device that supplies the dialysate, supplied from the dialysate supplying device, to the blood purifier.

3. The blood purification system according to claim 1, wherein the supplying mechanism includes a water treatment device that produces clean water; and the blood purification mechanisms include the personal dialysis device that produces a dialysate with a predetermined concentration by using the clean water supplied from the water treatment device and supplies the dialysate to the blood purifier.

4. The blood purification system according to claim 1, wherein the supplying mechanism includes a water treatment device and a dissolving device, the water treatment device produces clean water and the dissolving device produces an undiluted dialysate with a predetermined concentration by using the clean water produced in the water treatment device; and the blood purification mechanisms include the personal dialysis device that produces a dialysate with a predetermined concentration by using the undiluted dialysate and the clean water, respectively, supplied from the dissolving device and the water treatment device and the personal dialysis device supplies the dialysate to the blood purifier.

5. The blood purification system according to claim 1, wherein when predetermined information is transmitted from the blood purification mechanisms, a predetermined operation is performed by the supplying mechanism.

6. The blood purification system according to claim 1, wherein information relating to an amount of cleaning water, an antiseptic solution or a displacing liquid that is required by each of the blood purification mechanisms is transmitted from the blood purification mechanisms to the supplying mechanism.

7. The blood purification system according to claim 6, wherein based on the required amount of the cleaning water, the antiseptic solution or the displacing liquid, a signal is transmitted from the blood purification mechanisms, and the supplying mechanism supplies the cleaning water or the antiseptic solution.

8. The blood purification system according to claim 1, wherein the supplying mechanism may display a history relating to cleaning, disinfecting or displacing in each blood purification mechanisms.

9. The blood purification system according to claim 1, wherein the supplying mechanism can detect an abnormality by comparing information of a liquid to be supplied to the blood purification mechanisms with the predetermined information transmitted from the blood purification mechanisms.

10. A blood purification system comprising:
multiple blood purification mechanisms including a blood purifier performing a blood purification treatment on a specific patient; and
a supplying mechanism including a device for receiving signals from each of the blood purification mechanisms, each blood purification mechanism provides a specific signal, the supply mechanism programmed to supply a dialysate, an undiluted dialysate, clean water or an antiseptic solution, each of the blood purification mechanisms receives its specific supply of the dialysate, undiluted dialysate, clear water or antiseptic solution in response to its specific received signal;
each multiple blood purification mechanism comprising a monitoring device or personal dialysis device programmed for sending the specific signals, the monitoring device or personal dialysis device sending the specific signals to the supply mechanism relating to the specific information including temperature, a pressure, a concentration, a flow rate, or time of a liquid that is supplied from the supplying mechanism to the blood purification mechanisms, the monitoring device or personal dialysis device enabling bilateral information communication between each of the blood purification mechanism and the supplying mechanism so that information is received from all of the blood purification mechanisms;
the supplying mechanism obtains information relating to an amount of the dialysate to be used from each blood purification mechanism, and it is determined whether the prepared amount of the dialysate produced by a dissolving device is sufficient or not on a basis of the information relating to an amount of the dialysate to be used obtained from each blood purification mechanism.

11. The blood purification system according to claim 10, wherein the supplying mechanism includes a dialysate supplying device that produces a dialysate with a predetermined concentration by using clean water and an undiluted dialysate; and the blood purification mechanism includes the monitoring device that supplies the dialysate, supplied from the dialysate supplying device, to the blood purifier.

12. The blood purification system according to claim 10, wherein the supplying mechanism includes a water treatment device that produces clean water; and the blood purification mechanisms include the personal dialysis device that produces a dialysate with a predetermined concentration by using the clean water supplied from the water treatment device and supplies the dialysate to the blood purifier.

13. The blood purification system according to claim 10, wherein the supplying mechanism includes a water treatment device and a dissolving device, the water treatment device produces clean water and the dissolving device produces an undiluted dialysate with a predetermined concentration by using the clean water produced in the water treatment device; and the blood purification mechanisms include the personal dialysis device that produces a dialysate with a predetermined concentration by using the undiluted dialysate and the clean water, respectively, supplied from the dissolving device and the water treatment device and the personal dialysis device supplies the dialysate to the blood purifier.

14. The blood purification system according to claim 10, wherein when predetermined information is transmitted from the blood purification mechanisms, a predetermined operation is performed by the supplying mechanism.

15. The blood purification system according to claim 10, wherein information relating to an amount of cleaning water, an antiseptic solution or a displacing liquid that is required by each of the blood purification mechanisms is transmitted from the blood purification mechanisms to the supplying mechanism.

16. The blood purification system according to claim 15, wherein based on the required amount of the cleaning water, the antiseptic solution or the displacing liquid, a signal is transmitted from the blood purification mechanisms, and the supplying mechanism supplies the cleaning water or the antiseptic solution.

17. The blood purification system according to claim 10, wherein the supplying mechanism may display a history relating to cleaning, disinfecting or displacing in each blood purification mechanisms.

18. The blood purification system according to claim 10, wherein the supplying mechanism can detect an abnormality by comparing information of a liquid to be supplied to the blood purification mechanisms with the predetermined information transmitted from the blood purification mechanisms.

* * * * *

UNITED STATES PATENT AND TRADEMARK OFFICE
CERTIFICATE OF CORRECTION

| | |
|---|---|
| PATENT NO. | : 10,183,106 B2 |
| APPLICATION NO. | : 14/093437 |
| DATED | : January 22, 2019 |
| INVENTOR(S) | : Harutoshi Okabe et al. |

It is certified that error appears in the above-identified patent and that said Letters Patent is hereby corrected as shown below:

In the Specification

<u>Column 5</u>
Line 62          "is" should be --1a--

<u>Column 11</u>
Line 28          "is" should be --1a--

Signed and Sealed this
Fourteenth Day of May, 2019

Andrei Iancu
*Director of the United States Patent and Trademark Office*